United States Patent [19]

Willer

[11] Patent Number: 4,485,237

[45] Date of Patent: Nov. 27, 1984

[54] INSENSITIVE POLYNITRAMINE COMPOUND

[75] Inventor: Rodney L. Willer, Ridgecrest, Calif.

[73] Assignee: The United States of America as represented by the Secretary of the Navy, Washington, D.C.

[21] Appl. No.: 473,300

[22] Filed: Mar. 8, 1983

[51] Int. Cl.³ .......................................... C07D 487/10
[52] U.S. Cl. ....................................... 544/231; 149/92
[58] Field of Search ........................... 149/92; 544/231

[56] References Cited

U.S. PATENT DOCUMENTS

| | | | |
|---|---|---|---|
| 2,895,944 | 7/1959 | Mark et al. | 544/231 |
| 3,903,087 | 9/1975 | Kato et al. | 544/231 |
| 3,917,719 | 11/1975 | Baldwin et al. | 568/708 |
| 3,933,926 | 1/1976 | Salter et al. | 568/710 |
| 4,110,136 | 8/1978 | Hershkowitz et al. | 149/47 |
| 4,142,927 | 3/1979 | Walker et al. | 149/194 |
| 4,346,222 | 8/1982 | Levins et al. | 149/92 |

OTHER PUBLICATIONS

Mar. ed., *Advanced Organic Chemistry*, 2nd ed. (1977), McGraw Hill, p. 580.
Evans, *Aust. J. Chem.* 20 (1967), pp. 1643–1661.
Willer, R., "Synthesis and Characterization of a New Insensitive High Energy Polynitramine Compound, 2,4,8,10-tetranitro-2,4,8,10-tetraazaspiro[5.5]undecane(TNSU)", Naval Weapons Center, TP 6353, Mar. 1982.
Evans, R. F., *Aust. J. Chem.*, vol. 20 (1967), pp. 1643–1661.

*Primary Examiner*—Donald G. Daus
*Assistant Examiner*—William A. Teoli, Jr.
*Attorney, Agent, or Firm*—Robert F. Beers; W. Thom Skeer

[57] ABSTRACT

The energetic compound 2,4,8,10-tetranitro-2,4,8,10-tetraazaspiro [5.5]undecane(TNSU) is disclosed. A general method of making 1,3-dinitroso-1,3-diazacycloalkanes in a one pot synthesis by the condensation of the diamine and formaldehyde, followed by conversion to the nitroso compound with nitrous acid. The general method also provides for the production of the tetranitroso precusor of TNSU.

2 Claims, No Drawings

INSENSITIVE POLYNITRAMINE COMPOUND

BACKGROUND OF THE INVENTION

1. Field of the Invention

This invention relates to a novel energetic compound. More particularly, this invention relates to the polynitramine compound 2,4,8,10-tetranitro-2,4,8,10-tetraazaspiro[5.5]undecane. Further, this invention relates to a method of preparing said polynitramine compound.

2. Description of the Prior Art

Trinitrotoluene (TNT) is a well known explosive. The development of other energetic compounds which have high thermal stability and low impact sensitivity is needed. Accordingly, the author of this specification has developed a high energy polynitramine compound with properties and performance comparable to TNT.

SUMMARY OF THE INVENTION

The energetic compound, 2,4,8,10-tetranitro-2,4,8,10-tetraazaspiro[5.5]undecane (hereinafter TNSU) is provided by this invention. The method of preparing TNSU involves the preparation of the tetranitroso intermediate 2,4,8,10-tetranitroso-2,4,8,10-tetraazaspiro[5.5]undecane followed by nitrolysis to TNSU. The preparation of the said tetranitroso intermediate is accomplished through a newly developed general route involving the reaction of an alpha omega diamine with formaldehyde to generate a 1,3-diazacycloalkane, followed by nitrosation to form a corresponding dinitroso compound.

OBJECTS OF THE INVENTION

It is an object of this invention to provide an energetic compound having a high thermal stability and low impact sensitivity.

It is a further object of this invention to provide a high yield method of preparing the energetic compound TNSU from the tetranitroso intermediate.

Still another object of the invention is to provide a general synthetic route for preparing 1,3-nitroso-1,3-diazacycloalkanes, including the tetranitroso intermediate 2,4,8,10-tetranitroso-2,4,8,10-tetraazaspiro[5.5]undecane.

These and other objects and advantages of the invention will become apparent from the following detailed description of the invention.

DESCRIPTION OF THE PREFERRED EMBODIMENT

The synthesis of TNSU was first attempted by the synthesis of tetrakis(nitraminomethyl)methane from tetrakis(aminomethyl)methane followed by condensation with two moles of formaldehyde under acidic conditions to give the desired TNSU. The synthesis of tetrakis(nitraminomethyl)methane followed standard methodology for the conversion of a primary amine to the corresponding primary nitramine involving a three step procedure. First, the tetraamine was protected by conversion to the corresponding acetamide, methyl or ethyl urethane. The protected amine was then nitrated using a mixture of nitric acid and acetic anhydride. Finally, the protecting group was removed under basic conditions and the primary nitramine tetrakis(nitraminomethyl)methane was generated upon acidification of the hydrolysis mixture.

Typical procedures for the condensation of alpha-omega-dinitramines with formaldehyde have called for the addition of the dinitramine to a 0° C. solution of paraformaldehyde in 85 to 90% sulfuric acid or the addition of the preformed mono-N-methylol derivative of the alpha omega dinitramine to a 0° C. solution of 85 to 90% sulfuric acid. Unfortunately, the application of both of these procedures to tetrakis(nitraminomethyl)methane gave poor results. No identifiable product could be isolated with the free nitramine. Using the N-methylol derivative procedure, the novel compound TNSU was isolated, but with the low yield of under 15%. The low yield of this route lead to the search for improved higher yield methods of synthesizing TNSU.

An improved method was found to produce TNSU with a yield of about 55%. First, the condensation of tetrakis(aminomethyl)methane with formaldehyde yielded 2,4,8,10-tetraazaspiro[5.5]undecane. While still in solution, this compound was then treated with nitrous acid to form 2,4,8,10-tetranitroso-2,4,8,10-tetraazaspiro[5.5]undecane. The tetranitroso derivative was isolated and then nitrolyzed to TNSU.

The condensation of tetrakis(aminomethyl)methane with formaldehyde can be carried out at room temperature. The addition of a sodium nitrite solution and a hydrochloric acid solution to the condensation mixture to produce the nitrous acid generally resulted in a slight exotherm. This reaction step can be carried out in the temperature range of 0°-25° C.

The chemical and physical properties of TNSU are given in Table I with a comparison to those of TNT. Detonation velocity and pressure were measured by the method of Kamlet et al., J. Chem. Phys., v. 48 (1968), pp 23–35.

TABLE I

|  | TNSU Measured | TNSU Predicted | TNT |
|---|---|---|---|
| Melting point | 242–244° C. | — | 80.6° C. |
| Density | 1.72 g/cc | 1.67 g/cc | 1.65 g/cc |
| Heat of formation | 5.0 Kcal/Mole | — | — |
| Detonation velocity | 7.85 mm/usec | 7.77 mm/usec | 6.900 mm/usec |
| Detonation pressure | 295 Kbar | 269 Kbar | 205 Kbar |
| Impact Sensitivity (2.5 kg Wt) | 60 cm | — | 70 cm |

The method used to produce the tetranitroso derivative has been further developed and shown useful for the synthesis of 1,3-dinitroso-1,3-diazacycloalkanes. The one pot synthesis involved the reaction of alpha omega diamines with formalin or formaldehyde followed by treatment with nitrous acid to form the 1,3-dinitroso-1,3-diazacycloalkane of the structure

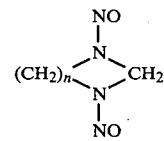

where n is an integer from 2 to 4.

It can be seen that the tetranitroso compound was prepared in similar fashion to the dinitroso compounds. With the tetramine, two equivalents of formaldehyde are used to prepare the tetranitroso derivative.

The following examples illustrate the novel methods and compounds without restricting the scope of the invention to what is specifically described.

EXAMPLE I

The general procedure for the synthesis of the 1,3-dinitroso-1,3-diazacycloalkanes is as follows:

The particular diamine (0.05 mole) was dissolved in 20 ml of distilled water. To this solution is added 3.28 g of 37% aqueous formaldehyde over five minutes. The solution is stirred for three hours at room temperature then is cooled to 0° C. by means of a salt-ice bath. A solution of 6.9 g (0.10 mole) of sodium nitrite dissolved in 20 ml of water is added. After five additional minutes of stirring 50 ml of 2N HCl is added over 30 seconds. (*Caution:* sometimes gas evolution and foaming occur at this point.) The mixture is stirred for one hour then the product is isolated by either filtering to remove the product (4) or extracting the solution with methylene chloride (3×100 ml) (1, 2, 3). In the latter cases the methylene chloride extracts were combined, dried over MgSO4, filtered, and the solvent removed at reduced pressure to give the crude products. The yields and physical properties of the produced 1,3-dinitroso-1,3-diazacycloalkanes and alkyl substituted 1,3-dinitroso-1,3-diazacycloalkanes are summarized below in Table 2.

TABLE 2

| Amine | 1,3-Dinitroso-1,3-Diazacycloalkane Product | | Yield | m.p. (°C.) |
|---|---|---|---|---|
| H2NCH2CH2NH2 | 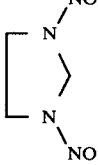 | (1) | 95 | 43–44 |
| H2N—(CH2)3—NH2 | 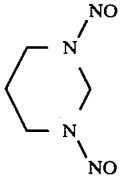 | (2) | 90 | 61–63 (lit 61.6–64.5) |
| H2N—(CH2)4—NH2 | 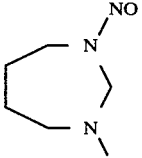 | (3) | 12 | 20 |
| C(CH2NH2)4 | 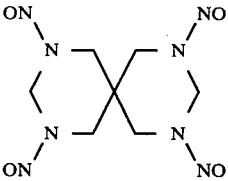 | (4) | 55 | 185–186 |
| H2NCH2CH(CH3)NH2 | 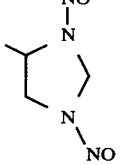 | (5) | 93 | (liq.) |
| H2NCH2CH2CH(CH3)NH2 | 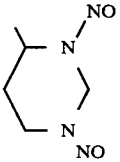 | (6) | 84 | (liq.) |

EXAMPLE 2

Tetrakis(Aminomethyl)Methane

The tetrabenzenesulfonyl derivative of pentaerythritol was prepared from pentaerythritol, benzenesulfonyl chloride, and pyridine in 95% yield as described by H. L. Herzog, "Pentaerythritol Tetrabromide", Org. Syn Coll., vol. IV (1963), p. 735)). The tetrabenzenesulfonate (34.8 g, 0.05 mole) was added to 200 ml of dry DMF and 16.25 g (0.25 mole) of sodium azide was added. The mixture was stirred at 120° C. for 16 hours. The mixture was cooled and diluted with 300 ml of ice water. The aqueous layer was then extracted with three 100-ml portions of ether. The combined ether extracts were back extracted with water (2×50 ml) and dried over $MgSO_4$. The solution was filtered and the ether removed at reduced pressure to yield the crude tetrakis-(azidomethyl)methane. *This compound is a very powerful explosive. When purified it has an impact sensitivity of 2 cm (2.5 Kg wt). It would not be purified unless due precaution is taken.* The crude tetraazide was dissolved in 200 ml of 95% ethanol and 1 gm of 10% Pd on C was added. The solution was hydrogenated for 12 hours with the main hydrogen tank shut off. Every 2 hours the bottle was vented to remove the accumulated $N_2$ and fresh hydrogen was introduced. No pressure drop was observed during the hydrogenation because the reduction of each azide requires one mole of hydrogen and releases one mole of nitrogen. The reaction can be monitored by working up an aliquot and examining the IR spectrum. The product was isolated by filtering the solution to remove the catalyst and removing the solvent at reduced pressure. The crude tetrakis(aminomethyl)methane weighed 6.2 g (0.047 mole, 94%).

NMR ($D_2O$, tsp)$\delta$=2.50 (s,1H, C$\underline{H}$), 4.70 (s,1H, N$\underline{H}$).

EXAMPLE 3

2,4,8,10-Tetranitroso-2,4,8,10-Tetraazaspiro[5.5]Undecane

Tetrakis(aminomethyl)methane (6.6 g, 0.05 mole) was dissolved in 20 ml of water. 7.56 of 37% aqueous formaldehyde solution was added to the mixture over 20 minutes. The solution was stirred at room temperature for 3 hours and then cooled to 0° C. A solution of sodium nitrite (13.8 g, 0.2 mole) in water (20 ml) was then added. When the temperature of the solution was 0° C., 100 ml of ice cold 2N HCl was added over 30 seconds. Considerable foaming and gas evolution occurred during the addition. The mixture was stirred at 0° C. for 1 hours and the crude product was collected by vacuum filtration and washed well with water. After drying, the product weighed 6.8–7.2 g (50–55% yield). The product melted with decomposition at 185°–186° C.

Analysis Calculated for $C_7H_{12}N_8O_4$: C, 30.88; H, 4.44; N) 41.17. Found: C, 31.14; H, 4.49; N, 41.24.

EXAMPLE 4

2,4,8,10-Tetranitro-2,4,8,10-Tetraazaspiro[5.5]Undecane

Ten ml of 98% nitric acid was cooled to −30° C. by means of a dicholorethane/dry ice slush and 1.0 g of the 2,4,8,10-tetranitroso-2,4,8,10-tetraazaspiro[5.5]undecane was added over 2 minutes. The dichloroethane bath was replaced with an ice/water bath and the mixture was stirred for 1 hour at 0° C. The ice water bath was removed and the mixture was stirred at room temperature for 15 minutes. The reaction was quenched by pouring into 15 g of ice. When the ice had melted, the product was collected and washed well with water. When dry it weighed 0.80–0.85 g (65–68% yield). The product can be recrystallized from DMF to give needles, m.p. 242°–244° C. (dec).

IR(KBr) 3000(w), 1550(vs), 1530(vs), 1450(m), 1430(s), 1370(s), 1315(m), 1275(sh), 1250(vs), 1210(sh), 1180(w), 1155(w), 1110(w), 1030(m), 1005(sh), 985(s), 950(m), 930(m), 910(w), 890(m), 865(w), 850(m), 815(w), 770(m), 760(m).

$^1$H NMR (DMSO—$d_6$) $\delta$=4.25 (s,2H, C—C$\underline{H_2}$N), 6.20 (s,1H, N—C$\underline{H_2}$—N).

Analysis calculated for $C_7H_{12}N_8O_8$: C, 25.00; H, 3.60; N, 33.33. Found: C, 25.18; H, 3.79;N, 33.20.

Obviously many modifications and variations of the present invention are possible in light of the above teachings. It is therefore to be understood that within the scope of the appended claims the invention may be practiced otherwise as specifically described.

What is claimed is:

1. 2,4,8,10-tetranitro-2,4,8,10-tetraazaspiro[5.5]undecane.
2. 2,4,8,10-tetranitroso-2,4,8,10-tetraazaspiro[5.5]undecane.

* * * * *